United States Patent
Strohalm (10) Patent No.: US 11,105,781 B2
(45) Date of Patent: Aug. 31, 2021

(54) METHOD FOR DETECTING THE LABELLING STATE OF UNKNOWN SPECIES OF MOLECULES

(71) Applicant: Thermo Fisher Scientific (Bremen) GmbH, Bremen (DE)

(72) Inventor: Martin Strohalm, Bremen (DE)

(73) Assignee: Thermo Fisher (Bremen) GmbH, Germering (DE)

( * ) Notice: Subject to any disclaimer, the term of this patent is extended or adjusted under 35 U.S.C. 154(b) by 253 days.

(21) Appl. No.: 16/425,013

(22) Filed: May 29, 2019

(65) Prior Publication Data
US 2019/0369067 A1 Dec. 5, 2019

(30) Foreign Application Priority Data
Jun. 1, 2018 (EP) .................................... 18175630

(51) Int. Cl.
G01N 30/72 (2006.01)
G01N 30/86 (2006.01)
G01N 30/88 (2006.01)

(52) U.S. Cl.
CPC ............. *G01N 30/72* (2013.01); *G01N 30/86* (2013.01); *G01N 30/88* (2013.01); *G01N 2030/8809* (2013.01); *G01N 2458/15* (2013.01)

(58) Field of Classification Search
CPC ........ G01N 30/72; G01N 30/86; G01N 30/88; G01N 2030/8809; G01N 2458/15; G01N 33/585; G01N 33/58; G01N 27/62; H01J 49/0027
See application file for complete search history.

(56) References Cited

U.S. PATENT DOCUMENTS

2009/0076737 A1* 3/2009 Wang ................. G06K 9/00543 702/23

FOREIGN PATENT DOCUMENTS

WO WO-2017044500 A1 3/2017

OTHER PUBLICATIONS

Extended European Search Report for Application No. 18175630.5, dated Jan. 2, 2019, 9 pages.
Valkenborg D., et al., "The Isotopic Distribution Conundrum," Mass Spectrometry Reviews, vol. 31, No. 1, May 16, 2011 (May 16, 2011), pp. 96-109, XP055021609, ISSN: 0277-7037, DOI: 10.1002/mas.20339.
Wittmann C., et al., "Mass Spectrometry for Metabolic Flux Analysis," Biotechnology and Bioengineering, vol. 62, No. 6, Mar. 20, 1999 (Mar. 20, 1999), pp. 739-750, XP055533163, ISSN: 0006-3592.
Yang T.H., et al., "Metabolic Network Simulation Using Logical Loop Algorithm and Jacobian Matrix," Metabolic Engineering, Academic Press, US, vol. 6, No. 4, Oct. 1, 2004 (Oct. 1, 2004), pp. 256-267, XP004607565, ISSN: 1096-7176, DOI:10.1016/J.YMBEN. 2004.02.002.
Notice of Reasons for Refusal dated May 13, 2021, to JP Application No. 2019-100179.

* cited by examiner

*Primary Examiner* — Jennifer Wecker
*Assistant Examiner* — Michael Paul Shimek (57) ABSTRACT

In one aspect, a method for detecting the labelling state of unknown species of molecules M contained in a sample exposed to a non-changing isotope labelling process using mass spectrometry is described.

6 Claims, 3 Drawing Sheets

METHOD FOR DETECTING THE LABELLING STATE OF UNKNOWN SPECIES OF MOLECULES

CLAIM TO PRIORITY

This application claims the benefit of European patent application no. EP18175630.5, entitled "Method for detecting the labelling state of unknown species of molecules," by Strohalm, and filed on Jun. 1, 2018. The content of the above-identified application is incorporated herein by reference in its entirety.

TECHNICAL FIELD

This disclosure relates to the methods for detecting the labelling state of unknown species of molecules M in a sample by mass spectrometry, when the sample was exposed to a non-changing isotope labelling process.

BACKGROUND

There is a big interest in science, medicine and several industries like pharma to understand chemical reaction processes in complex samples comprising an amount of various species of molecules. Such samples can be, in particular, biochemical samples like cells, blood, tissues, and bacteria. In particular, to understand the chemical reaction and the reaction pathways, an isotopic marker can be supplied to the sample of interest by the technology of isotopic labelling. An isotopic marker of an isotope labelling process may at least include one species of molecule, which might comprise various elements. This species of molecule, named in this patent application a labelled species of molecule of the isotopic marker, can be labelled by enrichment of a specific isotope $^xE$ of at least one specific element E of the molecule, which has in nature a low abundance, a marking isotope. For example, in a molecule comprising carbon atoms the isotope $^{13}C$ can be enriched. In another example, a labelled species of molecule can be labelled by enrichment of a specific isotope $^xE_1$ of the element $E_1$ and a specific isotope $^yE_2$ of the element $E_2$, wherein both elements $E_1$ and $E_2$ are comprised in the labelled species of molecule.

Enrichment of a specific isotope $^xE$ in a labelled species of molecule in general means that one or several atoms of the specific element E are replaced by the specific isotope $^xE$ in the labelled species of molecule.

In a particular embodiment of the isotope labelling process, in this patent application, named a single enriched isotope labelling process, this enrichment is done by only exchanging one atom of the specific element E of the labelled molecule with specific isotope $^xE$.

In a specific labelling process, in this patent application named a single isotope labelling process, the supplied isotopic marker is only comprising labelled species of molecules, in which only a specific isotope $^xE$ of only one specific element E is enriched. This enrichment may replace one or several atoms of the specific element E or are replaced by the specific isotope $^xE$.

Preferably, the isotopic marker is only comprising one labelled species of molecules, but it can also be several different species of molecules. Then in all these molecules, the isotope $^xE$ is enriched by replacing only atom of the element E in the molecules.

In other specific isotope labelling processes, the supplied isotopic marker is only comprising labelled species of molecules, in which a specific isotope $^xE$ of at least one specific element E enriched and this enrichment is done by only exchanging small number of atoms of the specific elements E in the labelled molecules with the specific isotope $^xE$. In one embodiment of these labelling processes, this enrichment is done by only exchanging up to 4 atoms of the specific elements E of the labelled molecule with the specific isotope $^xE$. In another embodiment of these labelling processes, this enrichment is done by only exchanging up to 3 atoms of the specific elements E of the labelled molecule with the specific isotope $^xE$. In a preferred embodiment of these labelling processes, this enrichment is done by only exchanging up to 2 atoms of the specific elements E of the labelled molecule with the specific isotope $^xE$. Preferably the isotopic marker is only comprising one labelled species of molecules, but it can also be several different species of molecules. Then in all these molecules the isotope $^xE$ are enriched by replacing only the small number of atoms E in the molecule. Preferably in more labelled species of molecules, the isotopes $^xE$ are enriched by replacing only one atom E in the molecule.

Preferably isotopic markers in the labelling processes are used, in which a certain portion of molecules of the labelled species of molecules are labelled. Typically this portion of molecules is higher than 50% of the amount of the molecules, but it can be in the range of 75% to 95%. E.g. 80% or 90% of species of the labelled molecule can be labelled.

If such specific isotopic markers can be administered to sample or a source of the sample, which can be an organism, different isotope labelling processes may happen. In some isotope labelling processes, in the following named non-changing isotope labelling processes, no new molecules are created due to the administration of the isotopic marker. Due to the administration of the isotopic marker in the molecules of the sample only the occurrence of the marking isotopes $^xE$ can be increased.

Different methods to label a sample with a non-changing isotope labelling process are known from prior art.

In particular isotope labelling processes, named in the this patent application non-changing single isotope labelling processes, the supplied isotopic marker is only comprising labelled species of molecules, in which only a specific isotope $^xE$ of only one specific element E is enriched and this enrichment is done by only exchanging atoms of the specific element E of the labelled molecule with specific isotope $^xE$ and no new molecules are created due to the administration of the isotopic marker. In such an isotope labeling process, the molecules of a labelled sample can be only labelled with the specific isotope $^xE$ and wherein each enrichment of the specific isotope $^xE$ in a molecule in the sample is based on a chemical reaction, in which a labelled molecule of the isotopic marker was involved and may be further based on chemical reactions of molecules of the sample, when at least two the molecules are already labelled by comprising the specific isotope $^xE$.

In a particular isotope labelling processes, named in this patent application as partially isotope labelling processes, the enrichment of the specific isotope $^xE$ of the at least specific element E in a molecule in the sample is based only on a chemical reaction, in which a labelled molecule of the isotopic marker was involved, wherein the labelled molecule does not transfer all its specific isotope $^xE$ of the at least specific element E to the resulting molecule in the sample.

There are different approaches known to detect the labelling state of various species of molecules contained in a sample, when non-changing isotope labelling process. In particular the labelling state can be detected by mass spectra of the sample, detected by a mass spectrometer.

One approach is only taking into account species of molecules in the sample, from which is known that they are contained in the sample in a certain amount so that they are detectable in mass spectra of the sample as mass peaks.

During the whole description the term "mass" will be used, when explaining mass spectra and measurements of a mass spectrometer. This term will be used in the broad sense of also encompassing the term mass to charge ratio (m/z). A mass spectrum in general is showing a detected intensity of signal I(p), which correlated to the number of detecting ions having a specific mass to charge ratio m/z which is correlated to a peak position p in the mass spectrum. The peak position can be to mass to charge ratio m/z but also other parameters like a frequency ω (e.g. in an Orbitrap mass spectrometer) or flight time (e.g. in a time-of-flight mass spectrometer). Only if all detected ions have the charge state z=1, the peak position is directly to the mass of ions. Otherwise not only ions of the mass m are detected at a specific m/z value but also ions of the mass n*m, when the ions have the charge state z=n. For the discussion of the techniques described herein, the detection of ions of different charge state z is no longer described in detail, but still possible in any measurement of a mass spectrometer.

For species of molecules in the sample, from which is known that they are contained in the sample, the labelling state of species of molecules can be detected by a targeted mode to detect the labelling state of the known species of molecules. Such targeted modes to detect the labelling state are known to the skilled person from the prior art. A species of molecules is known for an investigator, of he has reliable information, that the species of molecules is contained in the sample. He can have this knowledge from the kind of investigated sample of from other experiments, he did before to investigate the sample.

Another approach is not based on the knowledge that specific only taking into species of molecules are contained in the sample. By such "untargeted approaches" the labelling state of any species of molecules contained in a sample can be detected. In particular, the labelling state of such species of molecules contained in a sample can be detected, which are unknown. A species of molecules contained in a sample is an unknown species of molecules contained in a sample, when there is no convincing information available for a person investigating the sample that the species of molecules is contained in the sample. So still a further experiment needed to give the information with a high probability that if a specific species of molecules is contained in a sample.

Also such untargeted modes to detect the labelling state are known to the skilled person from the prior art and they can just detect the labelling state of an unknown species of molecules in the sample. But these approaches have many uncertainties and are using a very complex and complicated evaluation process.

Methods to identify elemental compositions of unknown species of molecules in a sample using mass spectrometry are known. In particular such a method is disclosed in the unpublished European patent application 18156903.9 of the applicant, which is hereby incorporated by reference in its entirety.

An object of this disclosure includes discussion regarding providing an improved method to detect the labelling state of species of molecules contained in a sample, which are unknown species of molecules, when a non-changing labelling process was applied to the sample. In particular, the method shall provide a more reliable result and shall reduce on the other the effort of the evaluation process. A further object of this disclosure discusses improving the reliability of the reaction flux analysis of the chemical reactions processes in complex samples, when non-changing isotope labelling processes are applied to the complex samples.

SUMMARY

The above-mentioned objects are solved by a new method for detecting the labelling state of unknown species of molecules M contained in a sample exposed to a non-changing single isotope labelling process using mass spectrometry according to claim 1.

The non-changing single isotope labelling process is using a specific isotope $^xE$ of a specific element E for labelling the molecules in the sample. The method comprises the following processes, which can be executed in different order.

In a process of the method at least one mass spectrum $I_{ul}(p_{ul})$ was measured of a reference sample with a mass spectrometer. This reference sample has not been exposed to the non-changing single isotope labelling process, to which the sample was exposed or has been only exposed to the non-changing single isotope labelling process at the beginning of the labelling process to which the sample was exposed before the measurement of at least one mass spectrum $I_{ul}(p_{ul})$.

The measured mass spectrum $I_{ul}(p_{ul})$ of the reference sample ("ul" means unlabelled sample) shows the abundance of the ionised ions given by a measured intensity I depending on their mass m (as explained above correctly mass to charge ratio) m/z, whereby this ratio is similar or related to the peak position p of the measured mass spectrum $I_{meas}(p)$. So, the measured mass spectrum $I_{ul}(p_{ul})$ contains the information about the mass m of all species of molecules M contained in the reference sample. In particular it contains the information about the mass m of all isotopologues of the species of molecules M.

The reference sample is correlated to the investigated sample, which is containing unknown molecules. It is the intention of the method to understand chemical reaction processes by the observation of the enrichment of the marking isotope $^xE$ in the sample due to the applied non-changing single isotope labelling process. To understand the progress of the labelling of the molecules and the accordingly reaction paths which result also from the transfer of the marking isotope $^xE$ from one molecule of the sample to another, it is still important to known what the species of molecules are contained in the sample before the non-changing single isotope labelling process was applied to the sample. So, the reference sample should provide this information.

In a preferred embodiment the sample itself can be used as reference sample. Then the at least one mass spectrum $I_{ul}(p_{ul})$ of the sample is measured with a mass spectrometer, before it is exposed to the non-changing single isotope labelling process or after it has been exposed to the non-changing single isotope labelling process only at the beginning of that labelling process.

In another preferred embodiment, the reference sample and the sample which is epoxied to the non-changing isotope labelling process are different portions of a common original sample, which is preferably a biochemical sample. So, reference sample and sample are subsets of the original sample. Preferably the original sample is a homogeneous system providing at most very small variations in its molecule composition. The reference sample can be taken from the original sample, after the original sample has been exposed to the non-changing single isotope labelling process only at the beginning of the labelling process.

In another embodiment, the sample exposed to the non-hanging labelling process and the reference sample can be different samples. But they can be provided by the same source, e.g. a living organism, a natural resource like a river or rocks, an industrial source, or an agricultural source. They can be also provided by different but correlated sources, like same living organism or same industrial production processes.

If at least one mass spectrum is measured of a reference sample, which has been only exposed to the non-changing single isotope labelling process at the beginning of said process, the time of exposure of the reference sample to the labelling process is so short, that no relevant labelling of the molecules with the specific isotope $^xE$ occurs, which would already detectable of the at least one measured mass spectrum. So, there are no further mass peaks detectable and no intensity shifts of the peak. In general, if a labelling is already detectable is correlated with the resolving power of the mass spectrometer executing the measurement. In instruments having a high resolving power and/or a high signal to noise ratio of the measured mass spectra the beginning labelling can be earlier detected. So, in the reference sample only a small amount of the molecules shall have been already labelled. Typically, not more than 5% of the molecules in the reference sample are labelled, preferably only 1% of molecules in the reference sample are labelled, and in particular preferably only 0.2% of molecules in the reference sample are labelled, In general, it is the goal, when measuring of the mass spectra of the reference sample to have mass spectra representing the unlabelled sample, the reference sample, to be able to identify elemental compositions of the molecules of the unlabelled sample from the mass spectra.

In a preferred embodiment the mass spectra of the reference sample are measured with an LC/MS instrument. Then the reference sample is provided to the mass spectrometer, in particular to its ion source, via a liquid chromatography system, in particular a liquid chromatography column. Then a series of mass spectra of the effluent of the liquid chromatography system is measured by the mass spectrum. This means at different times of the elution of the effluent is provided to the mass spectrometer, in particular it ion source to measure a mass spectrum at a specific elution time. Then from the series of mass spectra mass traces can be derived. According to the chromatography process, chromatographic peaks of can be detected at specific elution times, also called according to the chromatographic process retention times, for each species of molecules, which can be shown at this time as a mass trace. Typically, the mass traces are detected at the mass of an isotopologue of the species of molecules but to coalescence effects the mass may deviate at some time periods of measuring the series of mass spectra. The detection of the such mass traces taking into account the coalescence effect is described in the unpublished European patent application 18170779.5 of the applicant, which is hereby incorporated by reference in its entirety.

In general, the measurement of the at least mass spectra of the reference sample can be repeated several times and e.g. then the mass spectra can be averaged to have an improved base for the determination of the elemental compositions of species of molecules contained in the reference sample with the described methods. Single measurements can be repeated or complete series of measurement, e.g. during the repetition of chromatographic experiments.

The at least one mass spectrum $I_{ul}(p_{ul})$ of the reference sample can be measured by a kind of mass spectrometer, independent on its resolving power. In particular, it is preferred to use a mass spectrometer of high resolution like a mass spectrometer having an Orbitrap® mass analyser or other electrostatic ion traps as mass analyser, a Fourier transform (FT) mass spectrometer, an ion cyclotron (ICR) mass spectrometer, or an multi reflection time of flight (MR-TOF) mass spectrometer. Other mass spectrometers which can preferably used are particularly time of flight (TOF) mass spectrometer and mass spectrometer with a HR quadrupole mass analyzer to measure the at least one mass spectrum of the reference sample.

In a further process of the methods the sample which shall be investigated is exposed to a non-changing isotope labelling process with intention to enrich in the molecules of the sample with a marking isotope $^xE$ of at least one specific element E. Beside of this the used non-changing one isotope labelling process does not change the species of molecules in the sample. Only the species of molecules contained in the isotopic marker are added to the sample. So beside of these species molecules the same species of molecules can be observed in the reference sample and the sample. In the sample the molecules can be labelled when the sample has been exposed to non-changing isotope labelling process. So, in the molecules of the sample the accordingly enrichment of the specific isotopes $^xE$ of the at least specific element E provided by the isotopic marker of non-changing isotope labelling process can be observed.

In particular, isotopic markers can be used for a non-changing isotope labelling process which adds no new species of molecules to the sample. So, the same species of molecules can be observed in the reference sample and the sample. This has the advantage that no further mass peaks will be detected in the mass spectra of the sample, which are not correlated to species of molecules added to the sample due to the administration of the isotopic marker. Further the administration of such an isotopic marker does not influence the reactions in the sample. In the sample the molecules can be labelled when the sample has been exposed to non-changing isotope labelling process. So, in the molecules of the sample the accordingly enrichment of the specific isotopes $^xE$ of the at least specific element E provided by the isotopic marker of non-changing isotope labelling process can be observed.

Further in a preferred embodiment, a non-changing single isotope labelling process is used, wherein the supplied isotopic marker may comprise labelled species of molecules, in which only one specific isotope $^xE$ of only one specific element E in enriched. This kind of labelling process offers an advantage to follow the labelling process in a sample with controllable manner, because the same species molecules are contained in the reference sample and the sample exposed to the in the non-changing single isotope labelling process and a labelling can be only happen with the provided marking isotope $^xE$, which is only provided by the isotopic marker on labelled molecules Further on in another preferred embodiment, a non-changing single enriched isotope labelling process is used, in which the enrichment is done by only exchanging one atom of the specific element E of the labelled molecule with the specific isotope $^xE$. This kind of labelling process offers advantage to follow the labelling process in a sample with controllable manner, because the same species molecules are contained in the reference sample and the sample exposed to the in the non-changing single isotope labelling process and a labelling can be only happen with the provided marking isotope $^xE$, which is only provided by the isotopic marker on labelled molecules, in which only one single atom of element E has been exchanged by marking isotope $^xE$.

The choice of the used isotope labelling process reduces the complexity of the labelling of the molecules of the sample. Resulting from choice the techniques could be found by the inventors taking into account the specific characteristics of the non-changing isotope labelling process. In a preferred embodiment in the supplied isotopic marker supplied by the non-changing isotope labelling process comprising the labelled species of molecules, in which only one specific isotope $^xE$ of at least one specific element E in enriched, not all molecules of species of labelled molecules are labelled. There is only an artificial abundance of the labelled molecules in the sample. Typically, more than 50% of all molecules of the species of labelled molecules are labelled in the isotopic marker (labelling rate 50%), preferably more 80% of all molecules of the species of labelled molecules, and particularly more than 90%, more preferred are labelling degrees of more than 95%, more than 98%, or even more than 99%. All molecules of the species are labelled molecules. This labelling rate of the isotopic marker reduces the costs of his production and is not critical for the detection of the labeling state of species of molecules in the sample because the labelling rate is taken into account as explained below.

In a further process, mass spectra $I_i(p_l)$ of the sample are measured with a mass spectrometer after the beginning of the non-changing isotope labelling process of the sample.

The intention of these measurements is to observe the labelling process of the molecules contained in the sample. By the labelling process with the time more and more of the molecules contain the specific isotope $^xE$ of the at least one element E, which are replacing in the molecule an atom of the at least one element E according its natural occurrence. Hereby should be mentioned that mostly there happens not really an exchange of an atom E with the specific isotope $^xE$. The labelled molecules contained in the sample comprising the specific isotopes $^xE$ are the result of chemical reactions, in which a labelled species of the isotope marker is involved resulting in an increase of the atoms of the specific isotopes $^xE$ in the composition of the labelled molecule of the sample or in which a before labelled molecule of the sample is involved resulting in an increase of the atoms of the specific isotopes $^xE$ in the composition of the labelled molecule of the sample up to number of the atoms of the specific elements E contained in the molecule of the sample before the labelling process. So, by these reactions molecules which already exist before in the same are created, in which now the number of atoms of the specific isotopes $^xE$ is increased. So, with the time in the sample during the non-changing single isotope labelling process the number of atoms of the specific isotopes $^xE$ is increasing in the molecules of the sample. This increase may vary for every species of molecules contained in the sample and for some molecules it may be observed an increase following by a decrease of the number of atoms of the specific isotope $^xE$. In a single enriched isotope labelling process, a molecule M comprising n atoms of the specific isotope $^xE$ is called n-times labelled molecule $M_l$ in this patent application. For each molecule in the sample its labelling process can be described by the intensity contribution $L_M(n)$ or relative abundance $c_M(n)$ of the n-times labelled molecule $M_l$ of all molecules having the same elemental composition as the unlabelled molecule M of the sample, if the enrichment of the specific isotope $^xE$ is not taken into account. The unlabelled molecule M—or called 0-times labelled molecule M—of the sample has the intensity contribution $L_M(0)$ and relative abundance $c_M(0)$. If in the elemental composition of unlabelled molecule M k atoms of the element E are contained, the highest possible labelled molecule is the n-times labelled molecule $M_l$ having the relative abundance $c_M(k)$. The sum of all relative abundances of species of molecules in the sample, having the same elemental composition as the unlabeled molecule M of the sample, if the enrichment of the specific isotope $^xE$ is not taken into account is equal to 1.

$$c_M(0)+c_M(1)+c_M(2)+\ldots+c_M(k-1)+c_M(k)=1$$

So, relative abundance $c_M(n)$ is the intensity contribution $L_M(n)$ of a n-times labelled molecule $M_l$, when the sum of the intensity contributions $L_M(n)$ of all variants of labelled molecules $M_l$ and the unlabeled molecule M is normalized to 1 and describes the ratio of each variant of a labelled molecule $M_l$ to the total number of molecules having the same elemental composition, which is number of the all variants of the labelled molecules $M_l$ and the unlabeled molecules M.

So, the labelling state of a species of molecules M is defined by intensity contribution $L_M(n)$, in particular the relative abundance $c_M(n)$, of its n-times labelled molecules $M_l$. n is between 0 (unlabeled molecule) and n. In some specific embodiments not all labelled molecules $M_l$ are taken into account, in particular when they have a very small relative abundance. Typically, this happens when a high number of atoms of the element E are replaced by the specific isotope $^xE$. Then only a smaller number of labelled molecule $M_l$ than k are taken into account.

In general, in an isotope labelling process, a molecule M comprising $n_i$ atoms of the specific isotope $^xE_i$ of w different elements $E_i$ is called a $(n_1, n_2, \ldots, n_w)$-times labelled molecule $M_l$ in this patent application. For each molecule in the sample its labelling process can be described by the intensity contribution $L_M(n_1, n_2, \ldots, n_w)$ or relative abundance $c_M(n_1, n_2, \ldots, n_w)$ of the $(n_1, n_2, \ldots, n_w)$-times labelled molecule $M_l$ of all molecules having the same elemental composition as the unlabeled molecule M of the sample, if the enrichment of the specific isotopes $^xE_i$ is not taken into account. The unlabeled molecule M—or called $(0, 0, \ldots, 0)$-times labelled molecule M—of the sample has the intensity contribution $L_M(0, 0, \ldots, 0)$ and relative abundance $c_M(0, 0, \ldots, 0)$. If in the elemental composition of unlabelled molecule M $k_i$ atoms of the element $E_i$ are contained, the highest possible labelled molecule is the n-times labelled molecule $M_l$ having the relative abundance $c_M(n_1, n_2, \ldots, n_i=k_i, n_w)$. The sum of all relative abundances of species of molecules in sample, having the same elemental composition as the unlabelled molecule M of the sample, if the enrichment of the specific isotope $^xE$ is not taken into account is equal to 1.

So, relative abundance $c_M(n_1, n_2, \ldots, n_w)$ is the intensity contribution $L_M(n_1, n_2, \ldots, n_w)$ of a $(n_1, n_2, \ldots, n_w)$-times labelled molecule $M_l$, when the sum of the intensity contributions $L_M(n_1, n_2, \ldots, n_w)$ of all variants of labelled molecules $M_l$ and the unlabeled molecule M is normalized to 1 and describes the ratio of each variant of a labelled molecule $M_l$ to the total number of molecules having the same elemental composition, which is number of the all variants of the labelled molecules $M_l$ and the unlabeled molecules M.

The at least one mass spectrum $I_i(p_l)$ of the sample can be measured by a kind of mass spectrometer, independent on its resolving power. In particular it is preferred to use a mass spectrometer of high resolution like a mass spectrometer having an Orbitrap® mass analyser or other electrostatic ion traps as mass analyser, a Fourier transform (FT) mass spectrometer, an ion cyclotron (ICR) mass spectrometer or an multi reflection time of flight (MR-TOF) mass spectrometer. Other mass spectrometers which can preferably be used are particularly time of flight (TOF) mass spectrometer and mass spectrometer with a HR quadrupole mass analyzer to measure the at least one mass spectrum of the reference sample.

In a preferred embodiment at least one mass spectrum $I_{ul}(p_{ul})$ of the reference sample and the at least one mass spectrum $I_l(p_l)$ of the sample can be measured with the same kind of mass spectrometer. It is further preferred to measure the at least one mass spectrum $I_{ul}(p_{ul})$ of the reference sample and the at least one mass spectrum $I_l(p_l)$ of the sample with the same type of mass spectrometer. In particular, it is preferred to measure the at least one mass spectrum $I_{ul}(p_{ul})$ of the reference sample and the at least one mass spectrum $I_l(p_l)$ of the sample with the same mass spectrometer.

In a preferred embodiment the mass spectra of the sample are measured with an LC/MS instrument. Then the sample is provided to the mass spectrometer, in particular to its ion source, via a liquid chromatography system, in particular a liquid chromatography column. Then a series of mass spectra of the effluent of the liquid chromatography system is measured by the mass spectrum. This means at different times of the elution of the effluent the effluent is provided to the mass spectrometer, in particular its ion source to measure a mass spectrum at a specific elution time. Then from the series of mass spectra mass traces can be derived. According to the chromatography process chromatographic peaks of can be detected at specific elution times, also called according to the chromatographic process retension times, for each species of molecules, which can be shown at this time as a mass trace. Typically, the mass traces are detected at the mass of an isotopologue of the species of molecules but to coalescence effects the mass may deviate at some time periods of measuring the series of mass spectra. The detection of such mass traces taking into account the coalescence effect is described in the unpublished European patent application 18170779.5 of the applicant, which is hereby incorporated by reference in its entirety.

In general, the measurement of the at least mass spectra of the reference sample can be repeated several times and e.g. then the mass spectra can be averaged to have an improved base for the determination of the elemental compositions of species of molecules contained in the reference sample. Single measurements can be repeated or complete series of measurement, e.g. during the repetition of chromatographic experiments.

In general, after the beginning of the non-changing isotope labelling process mass spectra $I_l(p_l)$ of the sample are measured a time period to observe the process of labelling the species of molecules M contained in the sample. In this time the time dependent enrichment of the specific isotope $^xE$ can be observed, which can be expressed by the time dependent relative abundance $c_M(n,t)$ of its n-times labelled molecules $M_l$ describing the labelling state of the species of molecule M at a specific time t, which may be time after the start of the non-changing single isotope labelling process of the sample.

In a further process one or more most likely elemental compositions $C_{M,i}(+0)$ of at least one unknown species of molecules M contained in reference sample based on the at least one measured mass spectrum $I_{ul}(p_{ul})$ of the reference sample are determined. Various methods are known for a skilled person to execute this determination process.

A species of molecules is defined as a class of molecules having the same molecular formula (e.g. water has the molecular formula $H_2O$ and benzene the molecular formula $C_6H_6$.) By the molecular formula of a species of molecules is the elemental composition of the species of molecules described. The molecular formula is listing all elements which are contained in the molecule by indicating the symbol of the elements according to the periodic table of chemical elements of IUPAC and is listing by the index on the right side of the symbol of the element to number of atoms of the element which the molecule is consisting of. So, for a simple example, a benzene molecule, which is having the molecular formula $C_6H_6$, is consisting of 6 carbon atoms (symbol C) and 6 hydrogen atoms (symbol H). Molecules having the same molecular formula may have different structural formulas due to different isomeric forms, which have different enantiomeric structures resulting in different physical, chemical and biological properties.

In the reference sample, no or no detectable labelling with the specific isotopes has happened. Therefore, each elemental composition from species of molecules M contained in the reference sample is described by the expression $C_{M,i}(+0)$, wherein +0 means, that there is no labelling for all w elements, for which a labeling is possible by the applied non-changing isotope labelling process ($n_1=0$, $n_2=0$ . . . , $n_w=0$). This notation is used during the whole patent application for unlabelled species of molecules and unlabelled molecules (to avoid long terms of 0).

Further on the index M in the expression $C_{M,i}(+0)$ is identifying the species of molecule M and the index i is related to the different investigated most likely elemental compositions. Typically, $C_{M,i}(+0)$ is the molecular formula of an elemental composition.

How much most likely elemental composition is taken into account may depend on the result of the determination process of the elemental compositions. In one preferred embodiment, only the one most likely elemental composition is taken into account. Then the index i of for all determined species of molecules only 1. In another embodiment, the number of most likely compositions further used in the method may dependent on a criterion of the likelihood of an elemental composition. In particular, of some possible elemental compositions having a much higher likelihood than others, only the elemental composition of the higher likelihood may be taken into account. The number of determined elemental compositions, which are then used in the following processes, may vary for each species of molecules.

It has to be pronounced that with the process to determine the elemental compositions also the composition of already known molecules of the reference sample can be verified. The techniques are still able to detect also the labelling state of known species of molecules M in the sample. In particular, these results can be also used when the techniques are part of a method to analyse the progress of labelling of the molecules in the sample due to the non-changing isotope labelling process. Such a method is often named flux analysis process. This term will be also used in this patent application.

In a preferred embodiment a process is to determine one or more most likely elemental compositions $C_{M,i}(+0)$ of at least one species of molecules M is used, which is disclosed in the unpublished European patent application 18156903.9 of the applicant, which is hereby incorporated with its complete disclosure.

In a further process for each determined one or more most likely elemental compositions $C_{M,i}(+0)$ of at least one unknown species of molecules M contained in the reference sample the corresponding species of molecules $M_l$ contained in the sample is detected in the measured mass spectra $I_l(p_l)$ of the sample.

This process comprises the following three substeps, which are executed for each identified one or more most likely elemental compositions $C_{M,i}(+0)$ of at least one unknown species of molecules M contained in the reference sample.

In a first substep of the process to detect the corresponding species of molecules $M_l$ contained in the sample for the elemental composition $C_{M,i}(+0)$ and at least one discrete labelled state $C_{M,i}(+n_1, +n_2, \ldots, +n_w)$ of said elemental compositions $C_{M,i}(+0)$ the isotope peak patterns $I_{M(+u1, +u2, \ldots, +uw),i}$ are determined.

Methods known to the skilled person are applied to determine the isotope peak patterns $I_{M(+u1, +u2, \ldots, +uw),i}$. Preferably the resolving power of the mass spectrometer measuring the mass spectra $I_l(p_l)$ of the sample is taken into account to determine the isotope peak patterns $I_{M(+u1, +u2, \ldots, +uw),i}$.

In a preferred embodiment, it is further taken into account for the determination of the isotope peak patterns $I_{M(+u1, +u2, \ldots, +uw),i}$, that in the isotopic marker used during the non-changing isotope labelling process, all molecules of a species of the labelled molecules are labelled. Therefore, the labelling rates of the isotopic markers are taken into account.

In a particular preferred embodiment, the isotope peak patterns $I_{M(+u1, +u2, \ldots, +uw),i}$ are determined in that way that for the $u_v$-times labelling of the discrete labelling state with the specific isotope $^xE_v$ of the element $E_v$, $u_v$ atoms of the element $E_v$ in a species of molecule are replaced by the specific isotope $^xE_v$ with the labelling rate of the element $E_v$. So, for example if the labelling rate of carbon is, that 80% of the carbon atoms are replaced by the specific isotope $^{13}C$, and the discrete labelling state is 3-times labelled with carbon, for 3 atoms in the labelled species of molecules 80% of the natural abundance C atoms are replaced by the specific isotope $^{13}C$.

In a second substep of the process to detect the corresponding species of molecules $M_l$ contained in the sample detectable masses $m_{Ml,m}$ of the corresponding species of molecules $M_l$ are determined for the elemental compositions $C_{M,i}(+0)$ using the isotope peak patterns $I_{M(+u1, +u2, \ldots, +uw),i}$ of the elemental composition $C_{M,i}(+0)$ and the at least one discrete labelled state $C_{M,i}(+n_1, +n_2, \ldots, +n_w)$ of said elemental composition $C_{M,i}(+0)$.

In the isotope peak patterns $I_{M(+u1, +u2, \ldots, +uw),i}$ of the elemental composition $C_{M,i}(+0)$ and the at least one discrete labelled state $C_{M,i}(+n_1, +n_2, \ldots, +n_w)$ of said elemental composition $C_{M,i}(+0)$ intensity peaks of the different isotopologues of the unlabelled elemental composition $C_{M,i}(+0)$ and each discrete labelled state $C_{M,i}(+n_1, +n_2, \ldots, +n_w)$ of said elemental composition $C_{M,i}(+0)$ can be observed. All intensity peaks of all the determined isotope peak patterns $I_{M(+u1, +u2, \ldots, +uw),i}$ are compared if they can be resolved against each other by the mass spectrometer measuring the mass spectra $I_l(p_l)$ of the sample, when they are detected by the mass spectrometer at the same time. Hereby, the resolving power and/or the mass tolerance of the used mass spectrometer is taken into account, and in particular when measuring the mass spectra $I_l(p_l)$ of the sample. For peaks which cannot be resolved, it is defined a common center of mass $m_{Ml,m}$ by taking into account the mass value of centre of the intensity peaks and/or the mass value at the top value of the intensity peaks and/or the maximum intensity of intensity peaks, preferable to normalized maximum intensity of intensity peaks. In a preferred embodiment, the mass value at the top value of the intensity peaks are weighted by normalized maximum intensity of intensity peaks and then averaged to determine the common center of mass $m_{Ml,m}$. Depending on the resolving power of the mass spectrometer, when measuring the mass spectra $I_l(p_l)$ of the sample, the fine structure of isotopologues can be distinguished. In this case, for each different isotopologues of the fine structure, separate detectable masses $m_{Ml,m}$ can be identified to detect the corresponding species of molecules $M_l$ contained in the sample in the following third substep.

In this third substep of the process to detect the corresponding species of molecules $M_l$ contained in the sample the isotope peak pattern $I_{Ml,m}$ of the corresponding species of molecules $M_l$ are determining for the elemental composition $C_{M,i}(+0)$ from at least one measured mass spectrum $I_l(p_l)$ of the sample at the determined detectable masses $m_{Ml,m}$ of the corresponding species of molecules $M_l$.

To achieve the isotope peak pattern $I_{Ml,m}$ of the corresponding species of molecules $M_l$, for determined detectable masses $m_{Ml,m}$ a mass window is defined around the detectable mass having preferably its center at the detectable masses $m_{Ml,m}$, in this patent application named as a mass channel of each detectable masses $m_{Ml,m}$. The mass window is defined by the resolving power and/or mass accuracy of the mass spectrometer, when the mass spectrometer is measuring the at least one measured mass spectrum $I_l(p_l)$ of the sample. Preferably mass window is defined to be the sum of the resolution and the mass accuracy of the mass spectrometer, when measuring the at least one measured mass spectrum $I_l(p_l)$ of the sample. Then the isotope peak pattern $I_{Ml,m}$ of the corresponding species of molecules $M_l$ is determined by looking for the mass channel of each detectable masses $m_{Ml,m}$, if there can be identified a mass peak in the measured mass spectrum $I_l(p_l)$ of the sample in the mass channel. Preferably a mass peak is identified, if it has very signal to noise ratio higher than a specific value, which is preferably 1.5, particular preferably 3. The isotope peak pattern $I_{Ml,m}$ of the corresponding species of molecules $M_l$ is given by the identified mass peaks. According to the experiment, the isotope peak pattern $I_{Ml,m}$ of the corresponding species of molecules $M_l$ can be detected for a single mass spectrum, a set of mass spectra or the mass spectra of complete chromatogram or a mass trace in a chromatogram. In particular, the isotope peak pattern $I_{Ml,m}$ can be determined at specific times of the labelling process to study the progress of the labelling process in the same (also called flux analysis) and to derive from this reaction paths of processes in the sample, e.g., natural process in a cell or the processes when a drug is provided to a cell.

In a further process for each identified one or more most likely elemental compositions of at least one unknown species of molecules M contained in the reference sample a labelling state of the corresponding species of molecules $M_l$ in the sample is determined from the measured mass spectra $I_l(p_l)$ of the sample.

The labelling state of the corresponding species of molecules $M_l$ in the sample can be described by its intensity contributions $L_M(n_1, n_2, \ldots, n_w)$ or relative abundances $c_M(n_1, n_2, \ldots, n_w)$ of the $(n_1, n_2, \ldots, n_w)$-times labelled molecule $M_l$ and the unlabelled molecule M.

In this process, the labelling state of the corresponding species of molecules $M_l$ in the sample of the elemental composition $C_{M,i}(+0)$ is determined by determining the intensity contributions $L_{M,i}(n_1, n_2, \ldots, n_w)$ of the unlabelled state of the elemental composition $C_{M,i}(+0)$ and the discrete labelled states $C_{M,i}(+n_1, +n_2, \ldots, +n_w)$, for which the isotope peak patterns $I_{M(+u1, +u2, \ldots, +uw),i}$ was determined by comparing for the each determined detectable mass $m_{Ml,m}$ of the corresponding species of molecules $M_l$ the peak intensity at the determined detectable masses $m_{Ml,m}$ in the determined isotope peak pattern $I_{Ml,m}$ of the corresponding species of molecules $M_l$ with the peak intensity of the determined detectable masses $m_{Ml,m}$ in the isotope peak patterns $I_{M(+u1, +u2, \ldots, +uw),i}$ of the elemental composition $C_{M,i}(+0)$ and the discrete labelled states $C_{M,i}(+n_1, +n_2, \ldots, +n_w)$, for which the isotope peak patterns $I_{M(+u1, +u2, \ldots, +uw),i}$ was determined.

Preferably the isotope peak patterns $I_{M(+u1, +u2, \ldots, +uw),i}$ of the elemental composition $C_{M,i}(+0)$ and the discrete labelled states $C_{M,i}(+n_1, +n_2, \ldots, +n_w)$, for which the isotope peak patterns $I_{M(+u1, +u2, \ldots, +uw),i}$ was determined, have to be normalised before the comparison. This normalisation has to be done typically in that way, that the integrated intensity of the whole isotope peak patterns $I_{M(+u1, +u2, \ldots, +uw),i}$ has for all isotope peak patterns the same value, which is preferably 1.

In a preferred embodiment the process determining for each identified one or more most likely elemental compositions of at least one unknown species of molecules M contained in the reference sample a labelling state of the corresponding species of molecules $M_l$ in the sample from the measured mass spectra $I_i(p_i)$ for the each determined detectable mass $m_{Ml,m}$ of the corresponding species of molecules $M_l$ the comparison is done by comparing the peak intensity at the determined detectable masses $m_{Ml,m}$ in the determined isotope peak pattern $I_{Ml,m}$ of the corresponding species of molecules $M_l$ with the linear combination of the intensity contributions $L_{M,i}(n_1, n_2, \ldots, n_w)$ of the unlabelled state of the elemental composition $C_{M,i}(+0)$ and the discrete labelled states $C_{M,i}(+n_1, +n_2, \ldots, +n_w)$ and the peak intensity at the expected detectable masses $m_{Ml,m}$ in the isotope peak patterns $I_{M(+u),i}$ of the elemental composition $C_{M,i}(+0)$ and the discrete labelled states $C_{M,i}(+n_1, +n_2, \ldots, +n_w)$, for which the isotope peak patterns $I_{M(+u1, +u2, \ldots, +uw),i}$ was determined.

Normally, the determination of the intensity contributions $L_{M,i}(n_1, n_2, \ldots, n_w)$ of the unlabelled state of the elemental composition $C_{M,i}(+0)$ and the discrete labelled states $C_{M,i}(+n_1, +n_2, \ldots, +n_w)$ by the comparison run into an overdetermined problem, for which an optimisation approach has to be used to find the most probable value for the intensity contributions $L_{M,i}(n_1, n_2, \ldots, n_w)$. Preferably methods of constrained optimisation can be used. A particularly preferred method for the determination is the non-negative least square fitting. Dependent on the labelling experiment other optimisation approaches may be more appropriate to determine the intensity contributions $L_{M,i}(n_1, n_2, \ldots, n_w)$.

As long as the different processes are not using the results of another process, all processes can be executed in any order of the processes and any of these sequences of the processes shall be encompassed by the description and the claimed inventive method.

Several of the processes of the inventive method can be supported computers and processors, being stand alone or connected or in a cloud system and by software to execute the processes.

In embodiments described in this application give examples of the inventive method. So, they can be realised by each embodiment alone or by a combination of several or all feature of the described embodiments without any limitations.

DETAILED DESCRIPTION OF PREFERRED EMBODIMENTS

Figure 1:
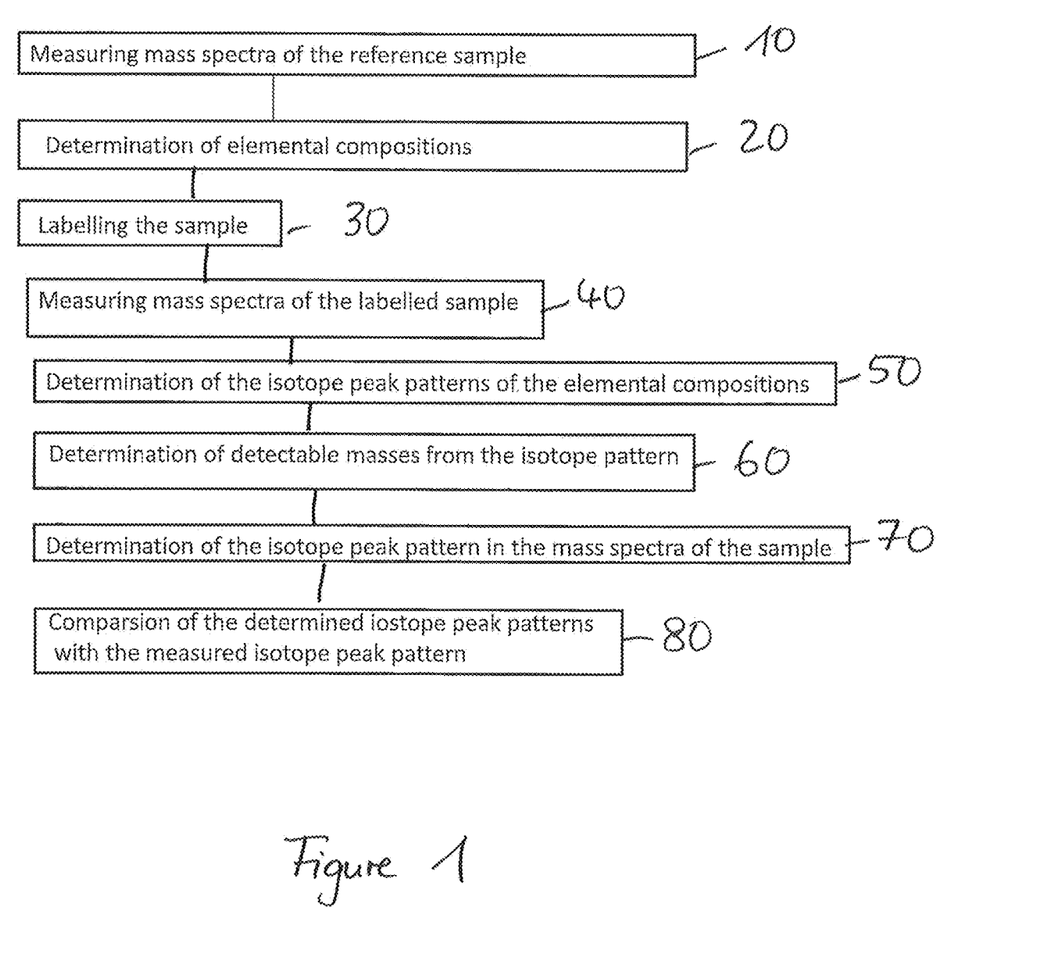
FIG. 1 shows a flow chart to illustrate the inventive method.

FIG. 1 shows in a flow diagram of one order how the processes of the inventive method can be executed. This is only an example of the inventive method.

Now shall be described another example of the method using a different order of the processes.

In this example as labelling process is used a single non-changing single enriched isotope labeling process using an isotopic marker which is labeled only with the specific isotope $^xE$.

In this example a homogeneous original sample, may be a bacteria culture, is divided at the beginning into to portions, a reference sample and a sample, which shall be labelled.

In a first step of the method mass spectra $I_{ul}(p_{ul})$ was measured of a reference sample with a mass spectrometer.

The mass spectra of the reference sample are measured with an LC/MS instrument. The reference sample is provided to the mass spectrometer, in particular to its ion source, via a liquid chromatography system, in particular a liquid chromatography column. Then a series of mass spectra of the effluent of the liquid chromatography system is measured by the mass spectrum. Then from the series of mass spectra mass traces can be derived. According to the chromatography process chromatographic peaks of can be detected at specific elution times, also called according to the chromatographic process retension times, for each species of molecules, which can be shown at this time as a mass trace. Typically, the mass traces are detected at the mass of an isotopologue of the species of molecules but to to coalescence effects the mass may deviate at some time periods of measuring the series of mass spectra. The detection of the such mass traces taking into account the coalescence effect is described in the unpublished European patent application 18170779.5 of the applicant, which is hereby incorporated with its complete disclosure.

The at least one mass spectrum $I_{ul}(p_{ul})$ of the reference sample can be measured by a kind of mass spectrometer, independent on its resolving power. In particular it is preferred to use a mass spectrometer of high resolution like a mass spectrometer having an Orbitrap® mass analyser.

In a further step of the inventive method the sample which shall be investigated is exposed to a non-changing single enriched isotope labelling process for a specific time period.

In the next step of the method mass spectra $I_i(p_i)$ of the sample are measured with the mass spectrometer, like a mass spectrometer having an Orbitrap® mass analyser after the beginning of the non-changing single enriched isotope labelling process of the sample.

The mass spectra of the sample are measured with an LC/MS instrument. Then the sample is provided to the mass spectrometer, in particular to its ion source, via a liquid chromatography system, in particular a liquid chromatography column. Then a series of mass spectra of the effluent of the liquid chromatography system is measured by the mass spectrum. This means at different times of the elution of the effluent the effluent is provided to the mass spectrometer, in particular its ion source to measure a mass spectrum at a specific elution time. Then from the series of mass spectra mass traces can be derived. According to the chromatography process chromatographic peaks of can be detected at specific elution times, also called according to the chromatographic process retension times, for each species of molecules, which can be shown at this time as a mass trace. Typically, the mass traces are detected at the mass of an isotopologue of the species of molecules but to coalescence effects the mass may deviate at some time periods of measuring the series of mass spectra. The detection of such mass traces taking into account the coalescence effect is described in the unpublished European patent application 18170779.5 of the applicant, which is hereby incorporated with its complete disclosure.

In general, after the beginning of the non-changing isotope labelling process mass spectra $I_l(p_l)$ of the sample are measured a time period to observe the process of labelling the species of molecules M contained in the sample. In this time the time dependent enrichment of the specific isotope $^xE$ can be observed, which can be expressed by the time dependent relative abundance $c_M(n,t)$ of its n-times labelled molecules $M_l$ describing the labelling state of the species of molecule M at a specific time t, which may be time after the start of the non-changing single isotope labelling process of the sample.

In the next step of the inventive method one or more most likely elemental compositions $C_{M,i}(+0)$ of at least one unknown species of molecules M contained in reference sample based on the at least one measured mass spectrum $I_{ul}(p_{ul})$ of the reference sample are determined.

In the method the only the most likely elemental composition $C_M(+0)$ of at least one species of molecules M is determined with the process, which is disclosed in the unpublished European patent application 18156903.9 of the applicant.

In the next step of the method for each determined most likely elemental compositions $C_M(+0)$ of at least one unknown species of molecules M contained in the reference sample the corresponding species of molecules $M_l$ contained in the sample is detected in the measured mass spectra $I_l(p_l)$ of the sample.

This process comprises the following three substeps, which are executed for each identified most likely elemental compositions $C_{M,i}(+0)$ of at least one unknown species of molecules M contained in the reference sample.

In a first substep of this process to detect the corresponding species of molecules $M_l$ contained in the sample for the elemental composition $C_M(+0)$ and all possible discrete labelled state $C_M(+n)$ of said elemental compositions $C_M(+0)$ the isotope peak patterns $I_{M(+u)}$ are determined.

Methods known to the skilled person are applied to determine the isotope peak patterns $I_{M(+u1, +u2, \ldots, +uw),i}$. The resolving power of the mass spectrometer measuring the mass spectra $I_l(p_l)$ of the sample is taken into account to determine the isotope peak patterns $I_{M(+u)}$.

Further on the labelling rates of the isotopic markers are taken into account in this determination.

In second substep of the process to detect the corresponding species of molecules $M_l$ contained in the sample detectable masses $m_{Ml,m}$ of the corresponding species of molecules $M_l$ are determined for the elemental compositions $C_M(+0)$ using the isotope peak patterns $I_{M(+u)}$ of the elemental composition $C_M(+0)$ and all discrete labelled state $C_M(+n)$ of said elemental composition $C_M(+0)$.

Hereby is taken account the resolving power and/or the mass tolerance of the used mass spectrometer.

For peaks which cannot be resolved, it is defined a common center of mass $m_{Ml,m}$ by taking into account the mass value at the top value of the intensity peaks and the maximum intensity of intensity peaks, preferable to normalized maximum intensity of intensity peaks. The mass value at the top value of the intensity peaks are weighted by normalized maximum intensity of intensity peaks and then averaged to determine the common center of mass $m_{Ml,m}$.

In this third substep of the process to detect the corresponding species of molecules $M_l$ contained in the sample the isotope peak pattern $I_{Ml,m}$ of the corresponding species of molecules $M_l$ are determining for the elemental composition $C_M(+0)$ from the measured mass spectra $I_l(p_l)$ of the sample at the determined detectable masses $m_{Ml,m}$ of the corresponding species of molecules $M_l$.

In the next step of the method for each identified most likely elemental compositions of at least one unknown species of molecules M contained in the reference sample a labelling state of the corresponding species of molecules $M_l$ in the sample is determined from the measured mass spectra $I_l(p_l)$ of the sample.

The labelling state of the corresponding species of molecules $M_l$ in the sample can be described for this method by its intensity contributions $L_M(n)$ or relative abundances $c_M(n)$ of the n-times labelled molecule $M_l$ and the unlabelled molecule M.

In this process the labelling state of the corresponding species of molecules $M_l$ in the sample of the elemental composition $C_M(+0)$ is determined by determining the intensity contributions $L_M(n)$ of the unlabelled state of the elemental composition $C_M(+0)$ and all discrete labelled states $C_M(+n)$ by comparing the peak intensity at the determined detectable masses $m_{Ml,m}$ in the determined isotope peak pattern $I_{Ml,m}$ of the corresponding species of molecules $M_l$ with the linear combination of the intensity contributions $L_M(n)$ of the unlabelled state of the elemental composition $C_M(+0)$ and the discrete labelled states $C_M(+n)$ and the peak intensity at the expected detectable masses $m_{Ml,m}$ in the isotope peak patterns $I_{M(+u)}$ of the elemental composition $C_M(+0)$ and the all discrete labelled states $C_M(+n_1)$.

For the determination of the intensity contributions $L_M(n)$ of the unlabelled state of the elemental composition $C_M(+0)$ and the discrete labelled states $C_M(+n)$ the non-negative least square fitting method is used.

Figure 2:
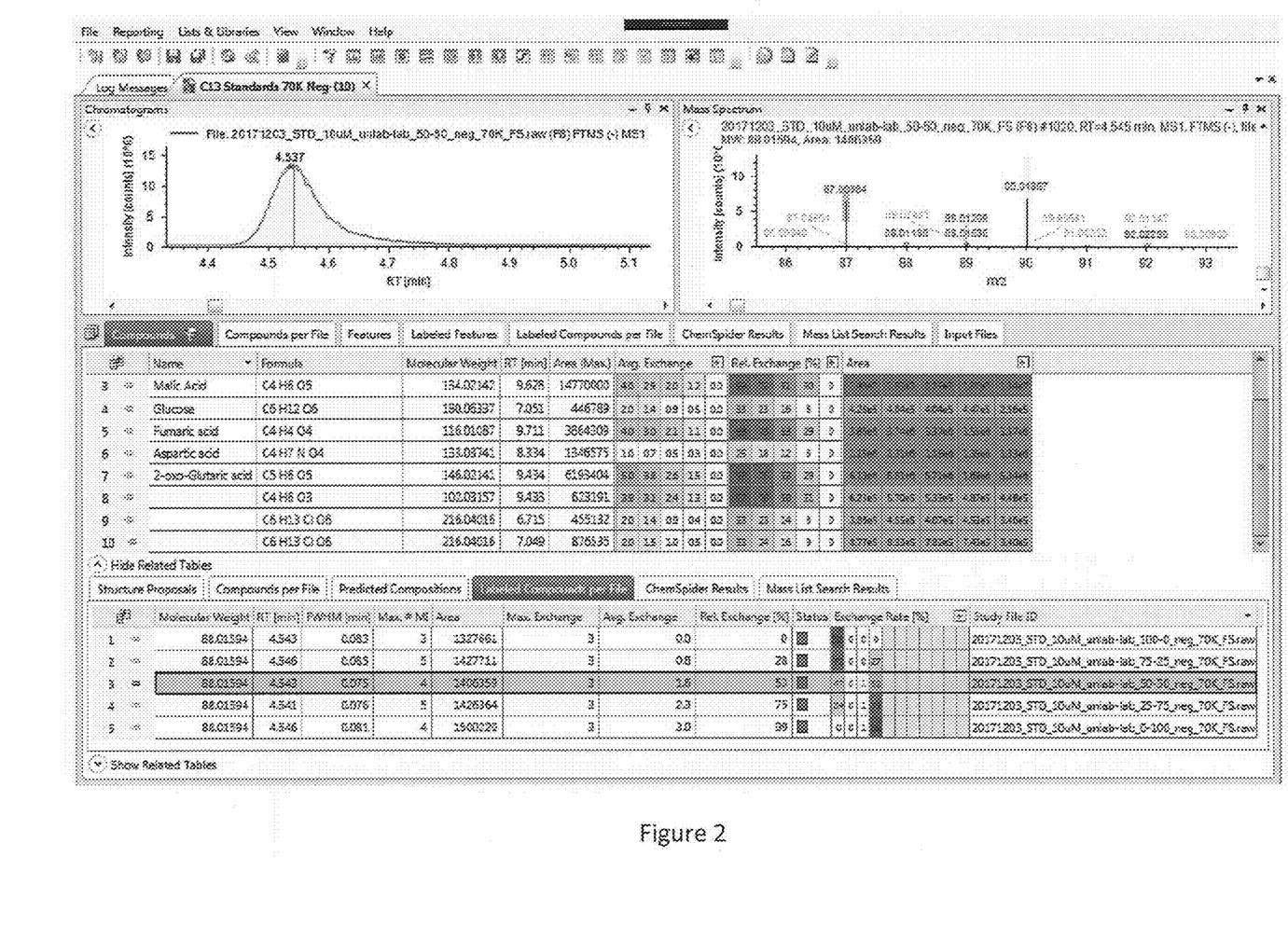
FIG. 2 shows the results of the inventive method applied to test samples having a defined labelling state
Figure 3:
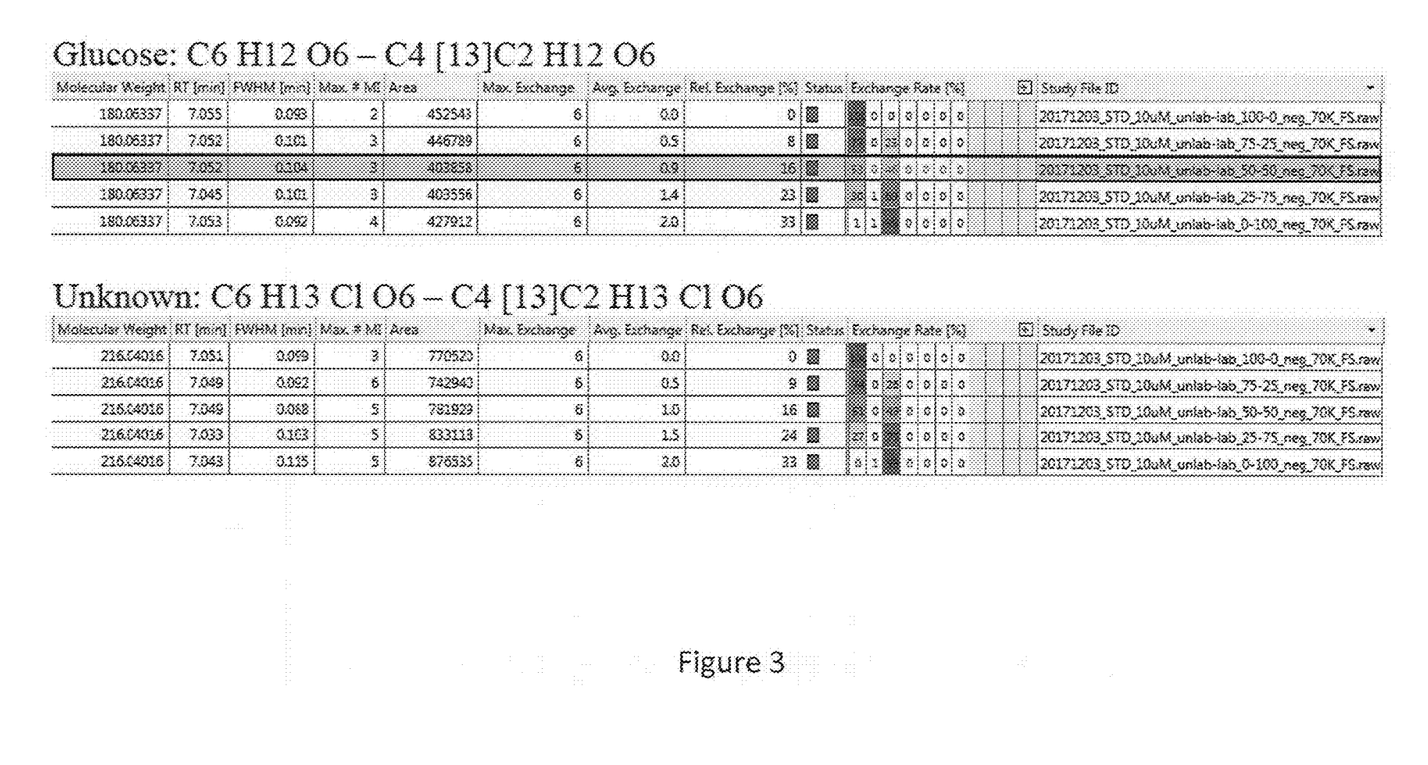
FIG. 3 shows the defined labelling states of two specific molecules in the test samples

In FIGS. 2 and 3 are shown test results proving the validity of the method. A test sample comprising several molecules is labelled with an isotope marker labelling with the specific isotope $^{13}C$. As shown in the right column of the table at the bottom of FIG. 2 several labelling states (0%, 25%, 50%, 75%, 100%) are investigated to different test samples. As shown in the middle of the sample the test sample is comprising several species of molecules. One species is glucose. For a molecule having the molecular weight 88.1094 in the columns under the title "Status exchange rate" the result for the determination of the labelling state with the method are shown. The intensity contributions of the discrete labelling states of the molecule are shown as percentage values. In the left of the three columns is shown the percentage of the unlabeled molecules and in each neighbouring column the percentage is shown, when one more specific isotope $^{13}C$ is contained in the molecules of the molecular weight 88.1094.

In FIG. 3 the same results are shown in the upper table for Glucose and in the lower table for another molecule with was found for the first time with the method, which identified the unknown molecule and determined its labelling state. The unknown molecule could be identified as an adduct of the Glucose with HCl.

The results show clearly that the method is able to identify the labelling state of the labelled test samples for the shown molecules.

The invention claimed is:

1. Method for detecting the labelling state of unknown species of molecules M contained in a sample exposed to a non-changing isotope labelling process using mass spectrometry comprising:

measuring at least one mass spectrum $I_{ul}(p_{ul})$ of a reference sample which has not been exposed to the non-changing isotope labelling process or has been only exposed to the non-changing isotope labelling process at the beginning of said process with a mass spectrometer;

labelling the sample in the non-changing isotope labelling process;

measuring, after the beginning of the non-changing isotope labelling process, mass spectra $I_l(p_l)$ of the sample with a mass spectrometer;

determining of one or more most likely elemental compositions $C_{M,i}(+0)$ of at least one unknown species of molecules M contained in the reference sample based on the at least one measured mass spectrum $I_{ul}(p_{ul})$ of the reference sample;

detecting, for each determined one or more most likely elemental compositions $C_{M,i}(+0)$ of at least one unknown species of molecules M contained in the reference sample, the corresponding species of molecules $M_l$ contained in the sample in the measured mass spectra $I_l(p_l)$ of the sample using for each identified one or more most likely elemental compositions $C_{M,i}(+0)$ of at least one unknown species of molecules M contained in the reference sample by:

determining for the elemental compositions $C_{M,i}(+0)$ and at least one discrete labelled state $C_{M,i}(+n_1, +n_2, \ldots, +n_w)$ of said elemental compositions $C_{M,i}(+0)$ the isotope peak patterns $I_{M(+u),i}$, determining for the elemental compositions $C_{M,i}(+0)$ detectable masses $m_{Ml,m}$ of the corresponding species of molecules $M_l$ using the isotope peak patterns $I_{M(+u1, +u2, \ldots, +uw),i}$ of the elemental composition $C_{M,i}(+0)$ and the at least one discrete labelled state $C_{M,i}(+n_1, +n_2, \ldots, +n_w)$ of said elemental composition $C_{M,i}(+0)$, determining for the elemental composition $C_{M,i}(+0)$ the isotope peak pattern $I_{Ml,m}$ of the corresponding species of molecules $M_l$ from at least one measured mass spectrum $I_l(p_l)$ of the sample at the determined detectable masses $m_{Ml,m}$ of the corresponding species of molecules $M_l$, determining for each identified one or more most likely elemental compositions of at least one unknown species of molecules M contained in the reference sample a labelling state of the corresponding species of molecules $M_l$ in the sample from the measured mass spectra $I_l(p_l)$ of the sample by:

determining for the elemental composition $C_{M,i}(+0)$ the intensity contributions $L_{M,i}(n_1, n_2, \ldots, n_w)$ of the unlabelled state of the elemental composition $C_{M,i}(+0)$ and the discrete labelled states $C_{M,i}(+n_1, +n_2, \ldots, +n_w)$, for which the isotope peak patterns $I_{M(+u1, +u2, \ldots, +uw),i}$ was determined, by comparing for the each determined detectable mass $m_{Ml,m}$ of the corresponding species of molecules $M_l$ the peak intensity at the determined detectable masses $m_{Ml,k}$ in the determined isotope peak pattern $I_{Ml,m}$ of the corresponding species of molecules $M_l$ with the peak intensity of the determined detectable masses $m_{Ml,m}$ in the isotope peak patterns $I_{M(+u1, +u2, \ldots, +uw),i}$ of the elemental composition $C_{M,i}(+0)$ and the discrete labelled states $C_{M,i}(+n_1, +n_2, \ldots, +n_w)$, for which the isotope peak patterns $I_{M(+u1, +u2, \ldots, +uw),i}$ was determined.

2. The method of claim 1, wherein in a time period after the beginning of the non-changing isotope labelling process mass spectra $I_l(p_l)$ of the sample are measured and in the time period for each identified one or more most likely elemental compositions of at least one species of molecules M contained in reference sample the labelling state of the unknown species of molecules M in the sample is determined from the measured mass spectra $I_l(p_l)$ of the sample.

3. The method of claim 1, wherein for all possible discrete labelled states the isotopic peak pattern are determined and used in the following steps of the method.

4. The method of claim 1, wherein for each identified one or more most likely elemental compositions of at least one unknown species of molecules M contained in the reference sample a labelling state of the corresponding species of molecules $M_l$ in the sample is determined from the measured mass spectra $I_l(p_l)$ of the sample by comparison for the each determined detectable mass $m_{Ml,m}$ of the corresponding species of molecules $M_l$ the linear combination of the intensity contributions $L_{M,i}(n_1, n_2, \ldots, n_w)$ of the unlabelled state of the elemental composition $C_{M,i}(+0)$ and the discrete labelled states $C_{M,i}(+n_1, +n_2, \ldots, +n_w)$ and the peak intensity at the expected detectable masses $m_{Ml,m}$ in the isotope peak patterns $I_{M(+u1, +u2, \ldots, +uw),i}$ of the elemental composition $C_{M,i}(+0)$ and the discrete labelled states $C_{M,i}(+n_1, +n_2, \ldots, +n_w)$, for which the isotope peak patterns $I_{M(+u1, +u2, \ldots, +uw),i}$ was determined with the peak intensity of the determined detectable masses $m_{Ml,m}$ in the isotope peak patterns $I_{M(+u1, +u2, \ldots, +uw),i}$ of the elemental composition $C_{M,i}(+0)$ and the discrete labelled states $C_{M,i}(+n_1, +n_2, \ldots, +n_w)$, for which the isotope peak patterns $I_{M(+u1, +u2, \ldots, +uw),i}$ was determined.

5. The method of claim 1, wherein the sample is labelled by a non-changing single enriched isotope labelling process.

6. The method of claim 1, wherein detecting the labelling state of unknown species of molecules M contained in the sample is used in flux analysis.

* * * * *

UNITED STATES PATENT AND TRADEMARK OFFICE
CERTIFICATE OF CORRECTION

| | |
|---|---|
| PATENT NO. | : 11,105,781 B2 |
| APPLICATION NO. | : 16/425013 |
| DATED | : August 31, 2021 |
| INVENTOR(S) | : Strohalm |

Page 1 of 1

It is certified that error appears in the above-identified patent and that said Letters Patent is hereby corrected as shown below:

In the Claims

Claim 1, Column 17, Line 11: replace "Method" with --A method--

Signed and Sealed this
Ninth Day of November, 2021

Drew Hirshfeld
*Performing the Functions and Duties of the
Under Secretary of Commerce for Intellectual Property and
Director of the United States Patent and Trademark Office*